United States Patent [19]

Seebach et al.

[11] Patent Number: 4,937,359
[45] Date of Patent: Jun. 26, 1990

[54] PROCESS FOR PREPARING (S)-4-METHYL-β-BUTYROLACTONE

[75] Inventors: Dieter Seebach, Zurich, Switzerland; Axel Griesbeck, Munich, Fed. Rep. of Germany

[73] Assignee: Imperial Chemical Industries plc, London, England

[21] Appl. No.: 324,023

[22] Filed: Mar. 16, 1989

Related U.S. Application Data

[62] Division of Ser. No. 104,205, Oct. 5, 1987, Pat. No. 4,835,294.

[30] Foreign Application Priority Data

Oct. 3, 1986 [GB] United Kingdom ............... 8623771

[51] Int. Cl.$^5$ .............................................. C07D 305/12
[52] U.S. Cl. ................................................... 549/328
[58] Field of Search ......................................... 549/328

[56] References Cited

U.S. PATENT DOCUMENTS 4,806,564 2/1989 Chabala et al. ................. 549/328

FOREIGN PATENT DOCUMENTS 0244143 11/1987 European Pat. Off. ............ 549/274

Primary Examiner—Nicky Chan
Attorney, Agent, or Firm—Cushman, Darby & Cushman

[57] ABSTRACT

The present invention relates to chemical compounds and in particular to substituted dioxanones obtained from (R)-3-hydroxybutyric acid. This invention also relates to a method for the production of such dioxanones and to processes using such dioxanones as starting-materials.

2 Claims, No Drawings

PROCESS FOR PREPARING (S)-4-METHYL-β-BUTYROLACTONE

This is a division of application Ser. No. 104,205, filed Oct. 5, 1987, now U.S. Pat. No. 4,835,294.

BACKGROUND OF THE INVENTION (R)-3-Hydroxybutyric acid is a readily available, cheap, chiral starting material useful in a number of synthetic methods, see for example Seidel et Seebach, Tet. Lett. 2209 (1984) and the references contained therein.

We have now discovered chemical intermediates, useful in the pharmaceutical and agrochemical industries, that can be prepared from (R)-3-hydroxybutyric acid.

THE INVENTION

The present invention provides a compound of the formula (I):

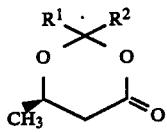

wherein $R^1$ is $C_{1-4}$ alkylamino or di-$C_{1-4}$ alkylamino and $R^2$ is hydrogen; or $R^1$ is $C_{1-4}$ alkoxy and $R^2$ is hydrogen, $C_{1-4}$ alkyl or $C_{1-4}$ alkoxy.

Suitably $R^1$ is di-$C_{1-4}$ alkylamino for example dimethylamino and $R^2$ is hydrogen.

More suitably $R^1$ is $C_{1-4}$ alkoxy for example methoxy or ethoxy and $R^2$ is hydrogen, $C_{1-4}$ alkyl for example methyl or ethyl or $C_{1-4}$ alkoxy for example methoxy or ethoxy.

In particular the present invention provides the dioxanones wherein $R^1$ is methoxy and $R^2$ is hydrogen, methyl or methoxy; and wherein $R^1$ and $R^2$ are both methoxy or ethoxy.

In another aspect of the present invention we provide a method for the production of a compound of the formula (I) wherein (R)-3-hydroxybutyric acid, of the formula (II), or a reactive derivative thereof is reacted with a compound of the formula (III):

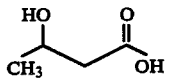

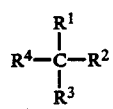

in which $R^1$ and $R^2$ are as defined hereinbefore and $R^3$ and $R^4$ are leaving groups.

Conveniently $R^3$ and $R^4$ are the same and are $C_{1-4}$ alkoxy groups. Of course such alkoxy groups are the same as, or better leaving groups than, any alkoxy groups $R^1$ and $R^2$. Typically $R^1$, $R^2$, $R^3$ and $R^4$ take the same value for example they are all methoxy groups or they are all ethoxy groups.

The reaction between the compounds of the formulae (II) and (III) is conveniently performed in an organic solvent, for example an aromatic hydrocarbon such as benzene or toluene, at ambient or an elevated temperature for example between 20° C. and 120° C. Typically methanol or ethanol or similar volatile by-product is removed from the reaction mixture by azeotropic distillation with the organic solvent.

As stated hereinbefore the compounds of the formula (I) have utility as chemical intermediates. According to a further aspect of the invention we provide a process for the production of (S)-4-methyl-β-butyrolactone of the formula (IV):

Wherein a compound of the formula (I) in which $R^1$ is $C_{1-4}$ alkoxy is subjected to the action of heat and low pressure. This compound is a well-known synthon in organic chemistry and is of potential utility in making polymers.

Typically the compound of the formula (I) is subjected to distillation at a temperature in the range 60° to 250° C. and a pressure in the range 0.1 to 75 torr. In general the higher the temperature the higher the pressure so that typical conditions, for the formation of (S)-4-methyl-b-butyrolactone from a compound of the formula (I) wherein $R^1$ is methoxy and $R^2$ is methyl, are 70°–75° C. at 0.15 torr; 120°–130° C. at 10 torr; and 180°–190° C. at 50 torr. The product is obtained together with unreacted starting-material.

A particular advantage of this process is that (S)-4-methyl-β-butyrolactone is generally obtained in an optical purity of greater than 98%.

According to a further aspect of the invention we provide a process for the production of a compound of the formula (V)

in which $R^5$ is a hydrocarbon residue wherein a compound of the formula (I) is reacted with an amine of the formula $R^5NH_2$.

Preferably $R^5$ contains an aromatic ring with benzylamine being especially suitable for the amine to be used in the reaction.

EXAMPLE 1

To a solution of (R)-3-hydroxybutyric acid (2.04 g) in benzene (15 ml) was added tetraethylorthocarbonate (3.84 g) in benzene (5 ml) at room temperature. The mixture was heated to 80° C. and the ethanol-benzene azeotrope was distilled until the heat temperature decreased to 50° C. The residue was evaporated under reduced pressure at 25° C./10 mbar to remove benzene to give a residue containing 2,2-dimethoxy-6-methyl-1,3-dioxan-4-one.

This residue was then subjected to distillation at 140°–160° C. mbar to afford (S)-4-methyl-β-butyrolactone (86%) with an optical purity of greater than 99% ($[x]_D^{25} = -27.9$ (c=3.3; CHCl$_3$)).

EXAMPLES 2–6

In a manner similar to Example 1 the following transformations were effected in benzene under reflux:

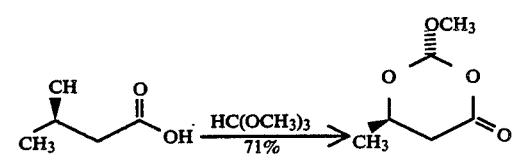

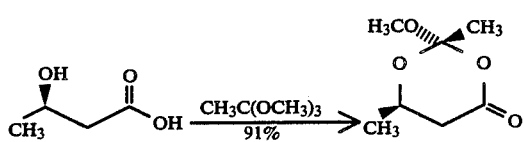

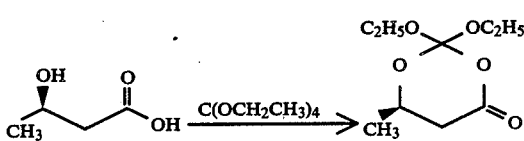

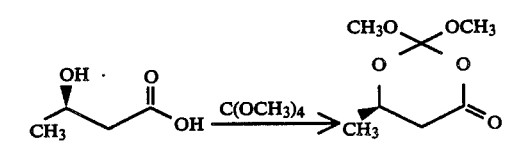

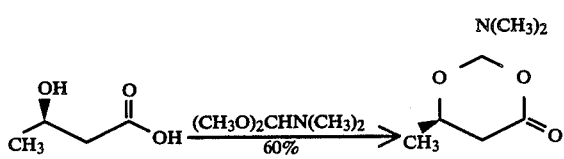

EXAMPLES 7–10

Distillation under the following conditions afforded (S)-4-methyl-b-butyrolactone; the remainder being unreacted starting-material.

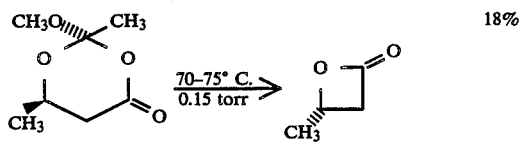 18%

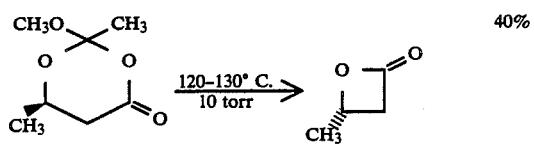 40%

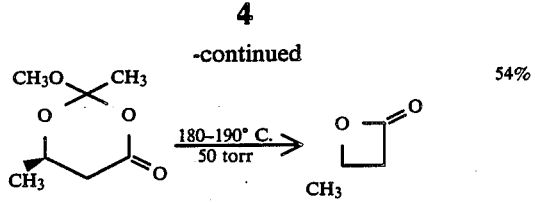 54%

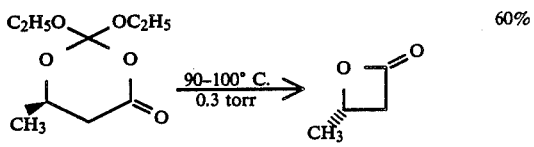 60%

EXAMPLE 11

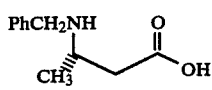

The product of Example 2, 2-methoxy-6-methyl-1,3-dioxan-4-one, was reacted with benzylamine in dichloromethane at room temperature for 24 hours. This afforded optically active 3-(N-benzylamino) butyric acid.

In a similar fashion the dioxanones of this invention can be reacted with a variety of amines.

We claim:

1. A process for the production (S)-4-methyl-β-butyrolactone of the formula (IV):

 (IV)

wherein a compound of the formula (I):

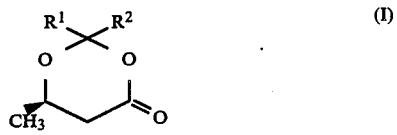 (I)

in which R¹ is $C_{1-4}$ alkoxy and R² is hydrogen, $C_{1-4}$ alkyl or $C_{1-4}$ alkoxy is subjected to distillation at a temperature in the range 60° to 250° C. and at a pressure in the range 0.1 to 75 torr.

2. A process according to claim 1 for the production of (S)-4-methyl-β-butyrolactone of the formula (IV) wherein the compound of the formula (I) is one in which R¹ is methoxy and R² is methyl.

* * * * *